(12) United States Patent
Nguyen et al.

(10) Patent No.: US 11,723,999 B2
(45) Date of Patent: Aug. 15, 2023

(54) AROMA CARTRIDGE, AROMA DISPLAY AND METHOD OF LOADING AND UNLOADING AROMA DISPLAY WITH AROMA CARTRIDGE

(71) Applicant: AROMAJOIN CORPORATION, Kyoto (JP)

(72) Inventors: Quang Van Nguyen, Kyoto (JP); Dong Wook Kim, Kyoto (JP); Kazuhiro Nakano, Kyoto (JP)

(73) Assignee: AROMAJOIN CORPORATION, Kyoto (JP)

( * ) Notice: Subject to any disclaimer, the term of this patent is extended or adjusted under 35 U.S.C. 154(b) by 449 days.

(21) Appl. No.: 17/068,887

(22) Filed: Oct. 13, 2020

(65) Prior Publication Data

US 2021/0128773 A1 May 6, 2021

(30) Foreign Application Priority Data

Oct. 30, 2019 (JP) ................................ 2019-196987

(51) Int. Cl.
*A61L 9/12* (2006.01)

(52) U.S. Cl.
CPC .............. *A61L 9/125* (2013.01); *A61L 9/122* (2013.01); *A61L 2209/133* (2013.01); *A61L 2209/134* (2013.01)

(58) Field of Classification Search
CPC .... A61L 9/125; A61L 9/122; A61L 2209/133; A61L 2209/134; A61L 2209/11; A61L 2209/15; A63J 2005/008
See application file for complete search history.

(56) References Cited

U.S. PATENT DOCUMENTS

| | | | |
|---|---|---|---|
| 2002/0158351 A1* | 10/2002 | Wohrle | ................... A61L 9/035 261/DIG. 89 |
| 2012/0080537 A1 | 4/2012 | Walter | |
| 2015/0283282 A1 | 10/2015 | Kim et al. | |
| 2018/0025864 A1 | 1/2018 | Katsuraku et al. | |
| 2018/0311392 A1 | 11/2018 | Kuijper | |
| 2020/0084411 A1 | 3/2020 | Kim | |

FOREIGN PATENT DOCUMENTS

| | | |
|---|---|---|
| CN | 108742140 A | 11/2018 |
| EP | 2 347 922 A2 | 7/2011 |
| JP | 07-041066 A | 2/1995 |

(Continued)

*Primary Examiner* — Sean E Conley
*Assistant Examiner* — Brendan A Hensel
(74) *Attorney, Agent, or Firm* — Keating and Bennett, LLP (57) ABSTRACT

An aroma cartridge 100 includes a columnar housing 360 consisting of upper and lower surfaces 362 and 364 parallel to and congruent with each other, and a side surface 366 formed to connect their circumferences. Housing 360 has a hollow portion in which a scent source is sealed. In the housing 360, an air feed inlet 220 communicating with the hollow portion and the outside of the housing, and a scent passage 300 are formed. The aroma cartridge 100 further includes a metal plate 240 of ferromagnetic body, fixed at least on a portion of the side surface 366. By providing a magnet on a cartridge loading section of the aroma cartridge, aroma display can be loaded/unloaded with aroma cartridge 100 easily and reliably.

10 Claims, 8 Drawing Sheets

(56) References Cited

FOREIGN PATENT DOCUMENTS

| | | |
|---|---|---|
| JP | 08-000423 A | 1/1996 |
| JP | 2013-543400 A | 12/2013 |
| JP | 2014-092673 A | 5/2014 |
| JP | 2017-097328 A | 6/2017 |
| JP | 6552696 B1 | 7/2019 |
| WO | 2017/156167 A1 | 9/2017 |

* cited by examiner

AROMA CARTRIDGE, AROMA DISPLAY AND METHOD OF LOADING AND UNLOADING AROMA DISPLAY WITH AROMA CARTRIDGE

CROSS-REFERENCE TO RELATED APPLICATION

The present application claims priority under 35 U.S.C. § 119(a) to Japanese Patent Application No. 2019-196987 filed in Japan on Oct. 30, 2019, the entire contents of which are hereby incorporated by reference.

BACKGROUND OF THE INVENTION

Field of the Invention

The present invention relates to an aroma display and, more specifically to an improvement of an aroma display that is capable of emission of various scents by holding a plurality of aroma cartridges.

Human communication is done in various modes based on human senses. Most frequently used are visual and auditory communications. By contrast, olfaction or sense of smell, on which we rely considerably in our lives, is hardly used in communication. However, if the sense of smell can be utilized in addition to visual and auditory senses, communication would be more effective and various people would be able to share their experiences more profoundly.

Focusing on this point, recently, devices have been proposed which are used with audio-visual reproducing devices such as television receivers, personal computers and game machines for generating scents fitting for the time and place. In the present Specification, such a device that generates scents fitting for scenes will be referred to as an "aroma display".

Such an aroma display cannot make full use of scents without the capability of freely selecting any one of a plurality of scents. For this purpose, one possible approach is to prepare a plurality of cartridges (referred to as "aroma cartridges") each containing a pre-selected scent emission source (referred to as a "scent source"), to load an aroma display with them and to cause the desired cartridge to emit the scent. US2015/0283282 discloses an aroma display of this type.

According to the disclosure of US2015/0283282, a scent channel for emitting the scent from the scent source in the cartridge is formed in the cartridge, and a mechanism for feeding air into the cartridge is provided in the aroma display. This mechanism causes the scent to be emitted outside through the scent channel. Separate from the mechanism for emitting scent from each cartridge, an air emitting mechanism, having an air discharging opening near the scent channels of the aroma cartridges held in the aroma display, is provided for discharging air free of any scent component. For switching scents after one scent is emitted, air is discharged from the air emitting mechanism to blow out the scented air therearound and then another scent is emitted. Thus, scents can be switched at any timing, avoiding improper blending of scents.

The aroma display having the above-described structure is capable of freely switching scents by selecting which air feeding mechanism is to be operated. Further, by operating the air emitting mechanism at that time, it is possible to prevent undesired blending of scents. The selection of air feeding mechanism to be operated and its timing may be controlled by sending an external command to the aroma display. Therefore, the aroma display can achieve magnificent effects of emitting desired scents fitting for the scenes by causing a desired air feeding mechanism or mechanisms to operate at desired timings of movies or animated films.

The aroma display disclosed in US2015/0283282, however, is disadvantageous in that it is rather troublesome to exchange aroma cartridges. According to the disclosure of US2015/0283282, the aroma display can be loaded with six aroma cartridges. An aroma cartridge has a triangular prism shape of which cross-section is a regular triangle. The aroma display has six holders each to be loaded with a cartridge, arranged at positions rotated by 60 degrees from each other about the center. Holders are of the same shape, having a wall separating each other and a slider provided on an outer side. By sliding the slider, the inner space of the holder is exposed, and it is loaded with an aroma cartridge. Then, the slider is slid back.

This process must be done every time an aroma cartridge is exchanged. This is troublesome. The above-described problem becomes more serious if the number of cartridges increases with which the aroma display can be loaded. Therefore, it is desirable to provide a mechanism allowing exchanging of aroma cartridges as simply and reliably as possible.

SUMMARY OF THE INVENTION

Therefore, an object of the present invention is to provide an aroma cartridge, an aroma display and a method of loading/unloading an aroma display with an aroma cartridge that enable easy and reliable exchange of aroma cartridges.

According to a first aspect, the present invention provides an aroma cartridge used with an aroma display capable of holding and releasing a plurality of aroma cartridges and emitting a scent or scents from any combinations of the plurality of aroma cartridges. The aroma display includes a housing having cartridge loading sections capable of holding the plurality of aroma cartridges, and a mechanism provided in the housing for causing the plurality of aroma cartridges held in the cartridge loading sections to emit scent individually. The cartridge loading section has an outer wall formed by a part of the housing and a bottom portion formed to be opposite to a bottom surface of the aroma cartridge held in the cartridge loading section. The bottom portion has an opening. The aroma display further includes a knock mechanism, provided in the housing opposite to the cartridge loading section with respect to the bottom portion, having a rod retractably inserted to the cartridge loading section through the opening formed at the bottom portion, fixing the rod alternately at a first position at which tip end of the rod protrudes by a first distance into the cartridge loading section and a second position at which tip end of the rod protrudes by a second distance smaller than the first distance, in accordance with pressure on the tip end of the rod, and a first body provided at that position of the outer wall of the cartridge loading section which corresponds to the position where the aroma cartridge is held. The aroma cartridge includes a columnar housing having a first and a second surface having outer shapes parallel to and congruent with each other and a side surface connecting outer circumferences of the first and second surface. A hollow portion is formed in the columnar housing in which a scent source is sealed. The columnar housing has formed therein a passage from the hollow portion to outside of the columnar housing and an air feed inlet for feeding air to the hollow portion from the outside of the columnar housing. The aroma cartridge further includes a second ferromagnetic body fixed on at least a portion of the side surface, and in response to feeding of air from the air feed inlet to the hollow portion, scented air from the scent source in the hollow portion is emitted through the passage to the outside.

Preferably, the outer shape has at least one corner; the passage has an opening close to the corner of the first surface; and the second ferromagnetic body is provided on the side surface opposite to the corner.

More preferably, the second ferromagnetic body is provided on the side surface of the columnar housing at a portion closer to the second surface than the first surface.

More preferably, the second ferromagnetic body is a metal plate containing iron.

According to a second aspect, the present invention provides an aroma display capable of holding and releasing a plurality of aroma cartridges and emitting a scent or scents from any combinations of the plurality of aroma cartridges. The plurality of aroma cartridges have ferromagnetic bodies on at least a part of their side surfaces. The aroma display includes: a housing having cartridge loading sections for holding the plurality of aroma cartridges; and a mechanism provided in the housing for individually causing each of the plurality of aroma cartridges held in the cartridge loading sections to emit scent. The cartridge loading section has an outer wall formed by a part of the housing and a bottom portion formed to be opposite to a bottom surface of the aroma cartridge held in the cartridge loading section, and the bottom portion has an opening. The aroma display further includes: a knock mechanism, provided in the housing opposite to the cartridge loading section with respect to the bottom portion, having a rod retractably inserted into the cartridge loading section through the opening formed at the bottom portion and an urging means urging the rod resiliently toward the cartridge loading section, fixing the rod alternately at a first position at which tip end of the rod protrudes by a first distance into the cartridge loading section and a second position at which tip end of the rod protrudes by a second distance smaller than the first distance, by the urging force from the urging means in accordance with pressure on the tip end of the rod; and a ferromagnetic body provided on the outer wall such that the ferromagnetic body is opposite to the ferromagnetic body of the aroma cartridge when the aroma cartridge is held in the cartridge loading section.

Preferably, the aroma cartridge is held by magnetic force between the ferromagnetic body of the aroma cartridge and the ferromagnetic body of the outer wall, with at least an upper end portion of the aroma cartridge released from the cartridge loading section and protruding from the cartridge loading section.

More preferably, the aroma cartridge is held by magnetic force between the ferromagnetic body of the aroma cartridge and the ferromagnetic body of the aroma display when a tip end of the rod is at the first position.

More preferably, the aroma cartridge is held by magnetic force between the ferromagnetic body of the aroma cartridge and the ferromagnetic body of the aroma display when a tip end of the rod is at the second position.

According to a third aspect, the present invention provides a method of loading and unloading a cartridge loading section of an aroma display with an aroma cartridge. A first ferromagnetic body is provided on a side surface of the aroma cartridge. The method of loading and unloading an aroma cartridge includes the steps of setting a rod at a first position by a knock mechanism, the knock mechanism being configured to alternately fix a tip end of the rod at the first and a second position, the tip end of the rod protruding by a first and a second distance from the bottom portion of the cartridge loading section at the first and a second position, respectively, the second distance being smaller than the first distance; pressing the rod by pushing an aroma cartridge into the cartridge loading section and thereby setting the tip end of the rod fixed at the second position by the knock mechanism and loading the cartridge loading section with the aroma cartridge; further pushing the aroma cartridge that has been held in the cartridge loading section with the tip end of the rod fixed at the second position, to return the tip end of the rod to the first position by a function of the knock mechanism, and thereby causing an upper end portion of the aroma cartridge to protrude from the cartridge loading section; causing, by a magnetic force between a second ferromagnetic body provided on an outer wall of the cartridge loading section and the first ferromagnetic body, the second ferromagnetic body to hold the aroma cartridge protruding from the cartridge loading section; and pulling the first ferromagnetic body strong enough to overcome the magnetic force to be separated from the second ferromagnetic body, and thereby removing the aroma cartridge from the aroma display.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

In the following description and in the drawings, the same components are denoted by the same reference characters.

Therefore, detailed description thereof will not be repeated. It is naturally understood that not every component of the embodiments described below is indispensable for the present invention. Components essential for implementing the present invention will be defined by the description of claims for the patent.

Embodiments

<Structure>

Figure 1:
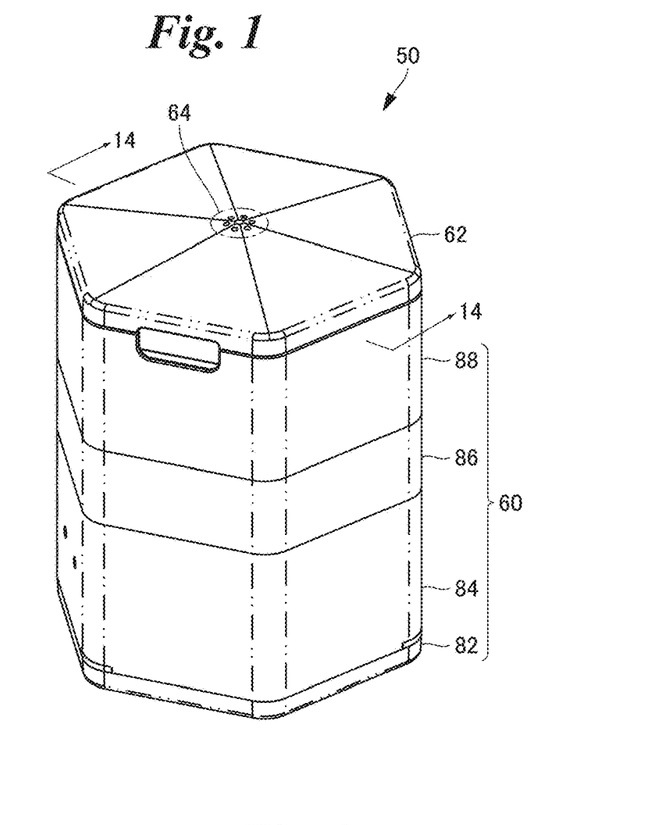
FIG. 1 shows an appearance of the aroma display in accordance with an embodiment of the present invention.

FIG. 1 shows an appearance of an aroma display 50 in accordance with an embodiment of the present invention. The aroma display 50 has a housing 60 that is of a substantially hexagonal columnar shape and a cap 62 detachably attached to an upper opening of housing 60.

Housing 60 includes: a base panel 82; a base body 84; a middle body 86; and an upper body 88 arranged above the base panel 82 in this sequence. Upper surface of cap 62 gradually rises toward its center. At the center of upper surface of cap 62, an opening area 64 is formed, where openings as outlets of scents emitted from aroma cartridges, which will be described later, are clustered together.

Figure 2:
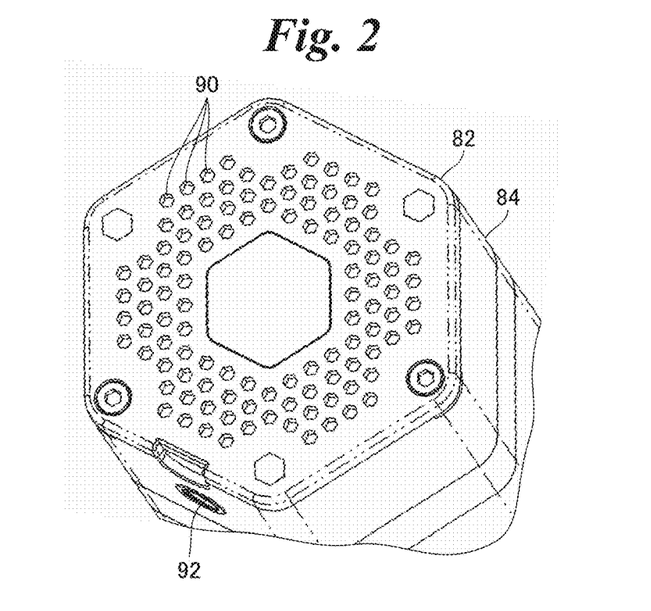
FIG. 2 is a perspective view showing a bottom surface of the aroma display shown in FIG. 1.

Referring to FIG. 2, entirely over the bottom surface of base panel 82, a large number of openings 90 are formed. These openings 90 are to take air used for emitting scents from aroma cartridges into housing 60. As can be seen from FIG. 2, a screw hole 92 is formed on one of the side surfaces of housing 60 in a size to meet an international standard so that a tripod can be fitted to aroma display 50.

Figure 3:
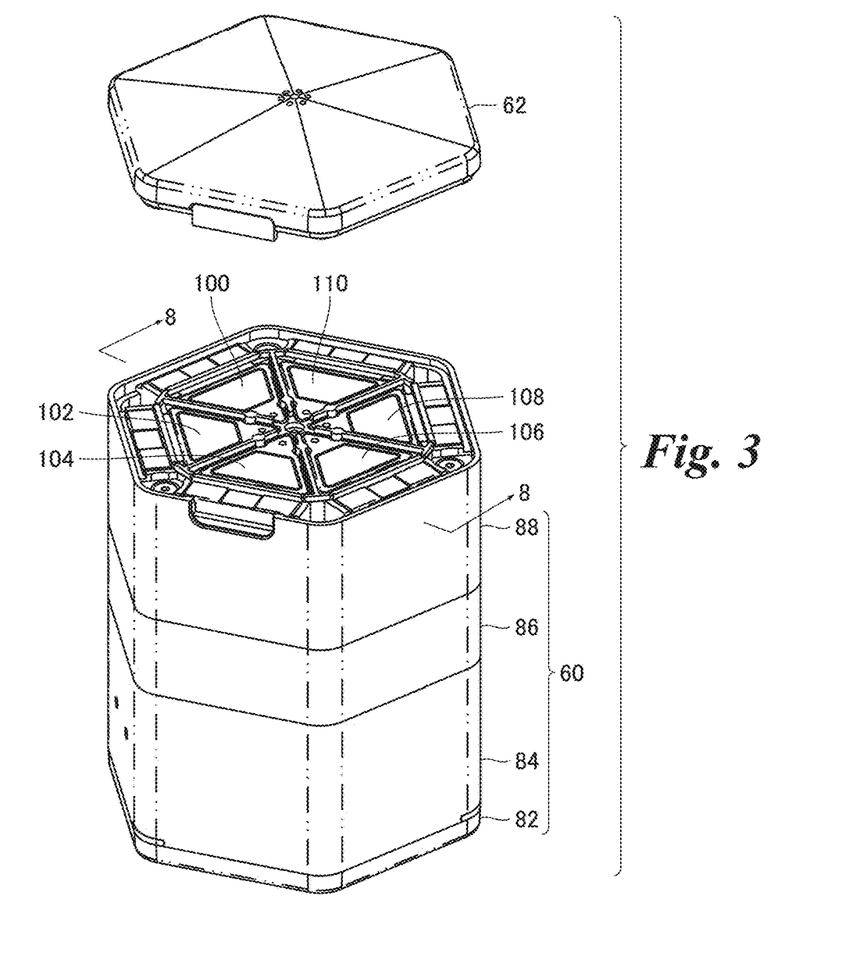
FIG. 3 shows the aroma display of FIG. 1 with its cap removed for exchanging an aroma cartridge.

FIG. 3 shows aroma display 50 of FIG. 1 with cap 62 removed from housing 60. Referring to FIG. 3, in the present embodiment, six aroma cartridges 100 to 110 are loaded in upper body 88. In FIG. 3, starting from aroma cartridge 100, aroma cartridges 102, 104, 106, 108 and 110 are held counter-clockwise in cartridge loading sections of upper body 88.

Figure 4:
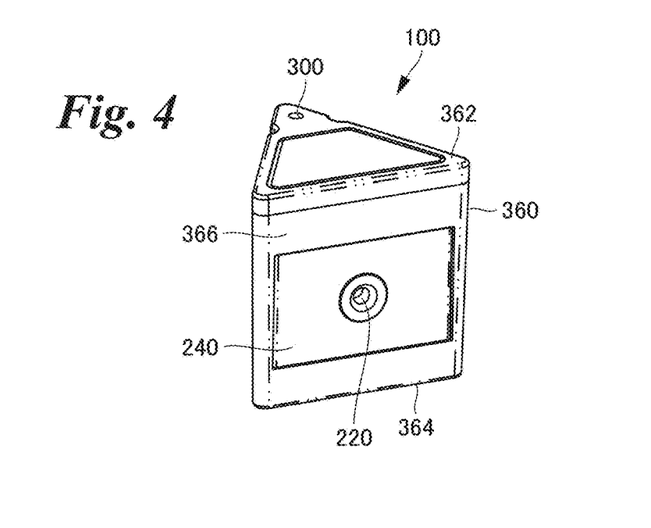
FIG. 4 is a perspective view from obliquely above the aroma cartridge.
Figure 5:
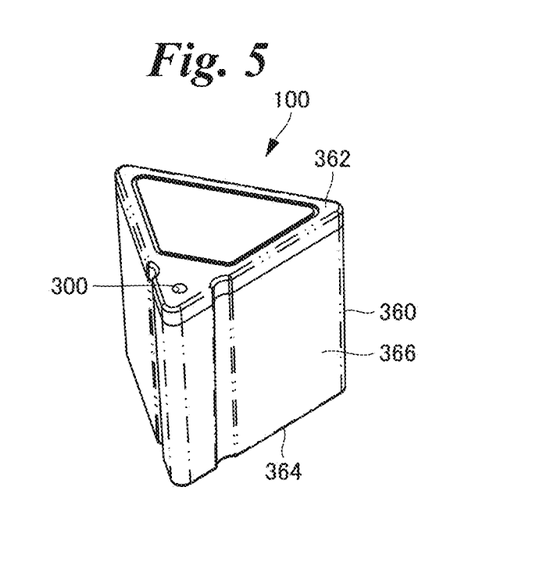
FIG. 5 is a perspective view from obliquely above the aroma cartridge, in a direction opposite to that of FIG. 4.

Referring to FIGS. 4 and 5, by way of example, an aroma cartridge 100 is a triangular prism of which cross-section is substantially a regular triangle. Specifically, aroma cartridge 100 has a housing 360 consisting of upper and lower surfaces 362 and 364, which are of regular triangular shapes parallel to and congruent with each other, and a side surface 366 formed to connect their circumferences. Housing 360 has a hollow portion in which a scent source is sealed. In the vicinity of one vertex on upper surface 362 of aroma cartridge 100, a scent passage 300 leading to the hollow portion of housing 360 is formed, through which air including scent from the scent source sealed in housing 360 is emitted. On a portion opposite to scent passage 300 of side surface 366, an air feed inlet 220 is provided for feeding air from an external micro blower to the inside of housing 360. A metal plate 240 formed of a ferromagnetic body is fixed around air feed inlet 220. The ferromagnetic body may include iron, cobalt, nickel, an alloy or an oxide that contains iron.

Figure 6:
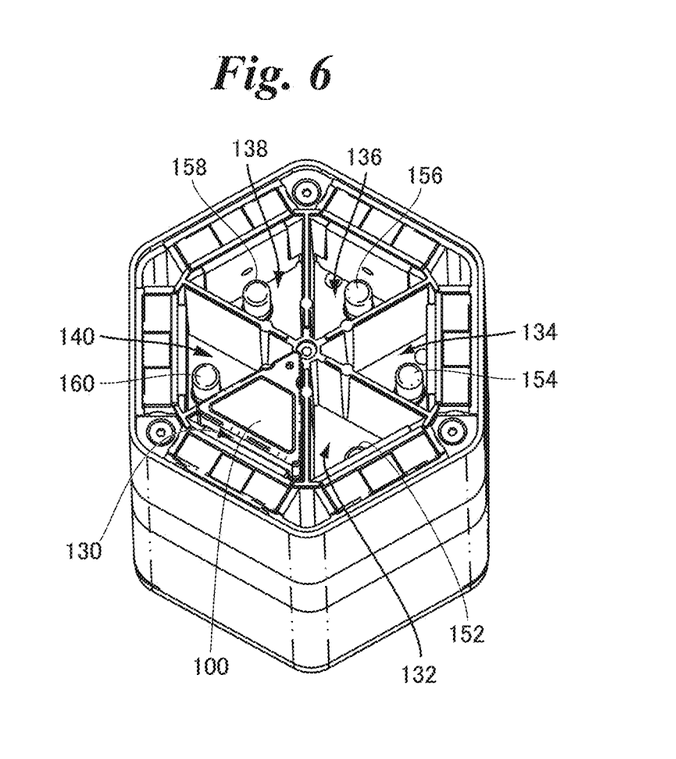
FIG. 6 is a perspective view of the cartridge loading sections of aroma display shown in FIGS. 1 and 2.
Figure 7:
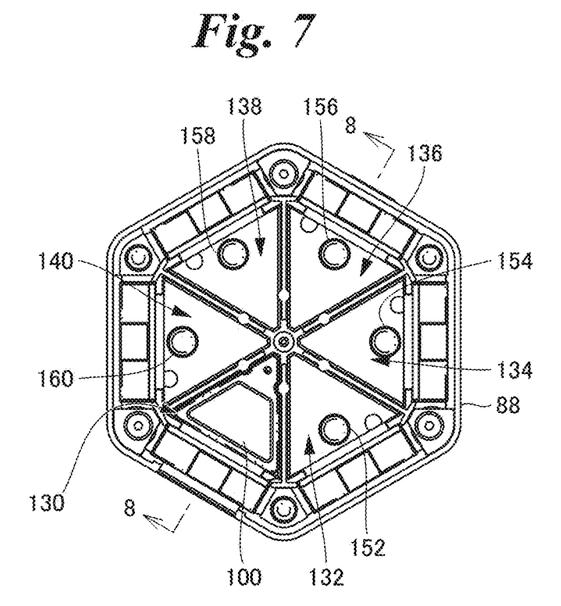
FIG. 7 is a plan view of the cartridge loading sections of aroma display shown in FIGS. 1 and 2.

FIGS. 6 and 7 shows upper body 88 with cap 62 removed from the upper portion. As will be described later, in the state shown in FIG. 6, upper edge of aroma cartridge 100 protrudes from the cartridge loading section. Referring to FIGS. 6 and 7, the space inside the upper body 88 is divided into six cartridge loading sections 130 to 140 which will be loaded with aroma cartridges 100 to 110, respectively. FIGS. 6 and 7 show aroma cartridge 100 only. Peeking out at the bottom of cartridge loading sections 130 to 140 are rods 150 to 160, which are part of a cam mechanism, not shown, enabling easy removal of aroma cartridges from the aroma display. The cam mechanism will be described later with reference to FIG. 8. In short, it has basically the same structure as a knock cam mechanism for a so-called click-action ball-point pen.

Figure 8:
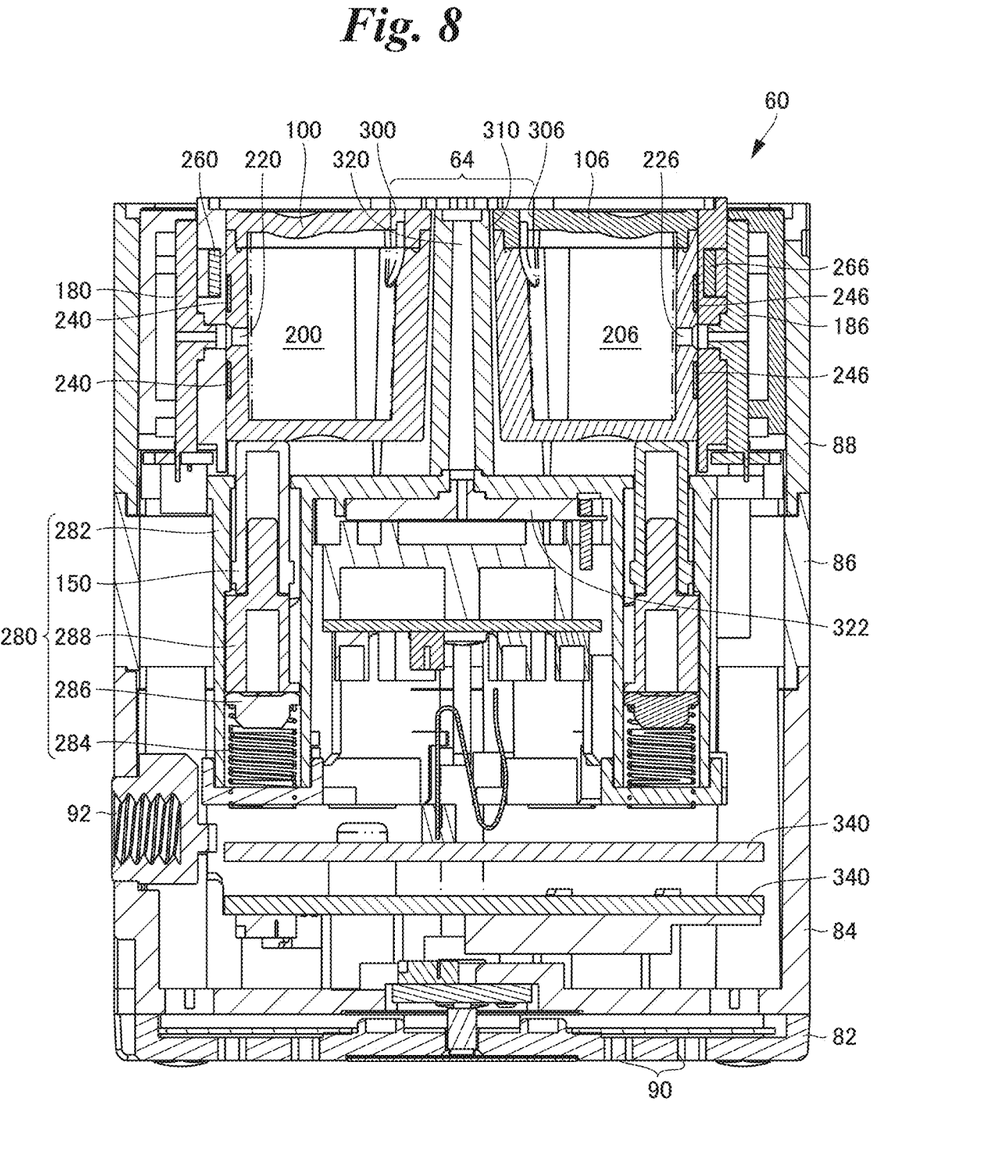
FIG. 8 is a cross-section of a housing of aroma display shown in FIG. 3, taken along 8-8.

Referring to FIG. 8, on the inner circumference of upper body 88, at a portion outside a cartridge loading section 130 (FIG. 6) which holds aroma cartridge 100, for example, a micro blower 180 utilizing a piezoelectric element is provided, which is driven by an external AC voltage, for feeding air to the hollow portion 200 inside aroma cartridge 100 through air feed inlet 220 formed on the back side of aroma cartridge 100. When air is blown into the hollow portion 200, air containing the scent of scent source sealed in the hollow portion 200 is emitted through scent passage 300 that opens towards opening area 64 formed at the center of the upper surface of cap 62 (FIGS. 1 and 3). Similarly, for aroma cartridge 106, a micro blower 186 is provided for feeding air to the hollow portion 206 inside aroma cartridge 106 through air feed inlet 226 formed on the back side of aroma cartridge 106, and when air is blown in to the hollow portion 206, air containing the scent of scent source sealed in the hollow portion 206 is emitted through scent passage 306 that opens towards opening area 64. The same applies to other cartridge loading sections. Therefore, by operating micro blowers 180 to 190 respectively, scents can be emitted individually from aroma cartridges 100 to 110.

At the center of upper body 88, a duct member 310 having an emission opening 320 leading to the opening area 64 is provided. At the bottom of duct member 310, a micro blower 322 is provided, which blows air taken from openings 90 formed at the bottom surface of base panel 82 into emission opening 320 and further blows out the air through opening area 64 to the outside of aroma display 50. Though micro blower 322 has a structure similar to that of, for example, micro blower 180 for the aroma cartridge, it has a larger size and it can blow out a larger amount of air than micro blower 180.

Within a wall of cartridge loading section above micro blower 180 provided corresponding to cartridge loading section 130, a magnet 260 is embedded, for temporarily holding aroma cartridge 100 when it is to be removed from cartridge loading section 130, by a magnetic force between magnet 260 and metal plate 240 of aroma cartridge 100. Likewise, within a wall of cartridge loading section 136 above micro blower 186, a magnet 266 is embedded. The same applies to other cartridge loading sections. These magnets are embedded in cartridge loading sections near to the inner circumference in order to ensure that sufficient magnetic force is exerted on the metal plates of aroma cartridges, so as to ease removal of the aroma cartridges and to prevent falling of the aroma cartridges.

By way of example, in a cartridge loading section in which aroma cartridge 100 is held (cartridge loading section 130 shown in FIG. 6), a knock mechanism 280 is provided for easy removal of aroma cartridge 100 from cartridge loading section 130. Knock mechanism 280 includes: a cylindrical cam body 282 closed at the bottom and opened at the top; a hollow rod 150 opened at the bottom, inserted into the upper portion of cam body 282, which protrudes long when knock mechanism 280 is extended and protrudes slightly when the mechanism 280 is contracted, into cartridge loading section 130; and a cylindrical solid rotor 288 having a protruding portion to be inserted from below into the opening of rod 150 and formed to have its shoulder abut against outer circumference of rod 150. A rotor holder 286 in contact with the lower end of rotor 288 is provided below rotor 288, and further below, a push-up spring 284 applying a force to rotor holder 286 constantly urging rotor holder 286 upward is provided. These structures are all provided inside cam body 282.

The hollow portion of cam body 282 has an approximately circular cross section. A plurality of protrusions is provided on the inner circumference at an upper portion of cam body 282 along the longitudinal direction of cam body 282. Two cam slopes in the same direction are formed at a lower surface of each of these protrusions. The recesses between these protrusions end at the upper end of cam body 282, and the inner circumference of cam body 282 is flush with the inner circumference of protrusions.

On a side surface of rotor 288, stop members of the same number as above-described protrusions are provided, each of which is of the width so that it is slidable in the recess, and upper end surface thereof forms a shoulder of rotor 288. At the upper end surface of a stop member, a cam slope is formed, which engages with one of the cam slopes mentioned above.

If aroma display 50 is facing upward whenever aroma cartridge 100 is removed, metal plates 240 and 246 as well as magnets 260 and 266 are unnecessary. Actually, however, aroma display 50 is not always facing upward when aroma cartridge 100 is removed or exchanged. For example, if aroma display 50 is hanging near the ceiling, aroma display 50 will face downward. In that case, if aroma cartridge 100 is to be removed using the above-described cam mechanism, aroma cartridge 100 would fall by its weight, unless metal plate 240 and magnet 260 and the like are provided. Further, when aroma display 50 is to be loaded with aroma cartridge 100, it is possible that aroma cartridge 100 slips down and falls accidentally. Therefore, in the present embodiment, by the combination of metal plate 240 and magnet 260, aroma cartridge 100 is held and prevented from falling even when aroma cartridge 100 is pushed out from upper body 88 by knock mechanism 280. By this arrangement, it becomes possible to easily exchange aroma cartridge 100 no matter in what posture aroma display 50 is held.

In order to maximize such an effect, metal plate 240 is desirably attached to the side surface of housing 360 and at least at a portion closer to the lower surface than to the upper surface. When aroma cartridge 100 released from cartridge loading section 130 by the operation of knock mechanism 280, aroma cartridge 100 can more securely be held by magnet 260 if metal plate 240 is provided at the lower portion of aroma cartridge 100. Naturally, metal plate 240 may be provided at a portion closer to the upper surface of aroma cartridge 100, as shown in FIG. 4.

As shown in FIG. 8, in base body 84, a control board 340 is provided for applying AC voltages to micro blowers 180 to 190 and micro blower 322 for their operation. Further, control board 340 is capable of communicating with an external control device through wireless communication, and it applies AC voltages to micro blowers 180 to 190 and 322 in accordance with a control signal transmitted from the external control device.

<Operation>

The above-described aroma display 50 operates as follows. To use aroma display 50, first, it is necessary to load upper body 88 with aroma cartridges 100 to 110. For this purpose, as shown in FIG. 6, the rod of each knock mechanism, such as rod 154 of cartridge loading section 134 and rod 156 of cartridge loading section 136, is initialized to the position protruding into the cartridge loading section. Here, the stop members of rotor 288 are in the recesses. By the force of push-up spring 284, rotor holder 286 and push-up spring 284 are integrally slid upward until the upper ends of stop members of rotor 286 abut the inner circumferences of upper edges of cam body 282. At this time, the lower end of rod 150 is in contact with the upper end of rotor 288 and, therefore, rod 150 also slides upward and its upper end protrudes into cartridge loading section 130. This position will be referred to as the first position.

Figure 11:
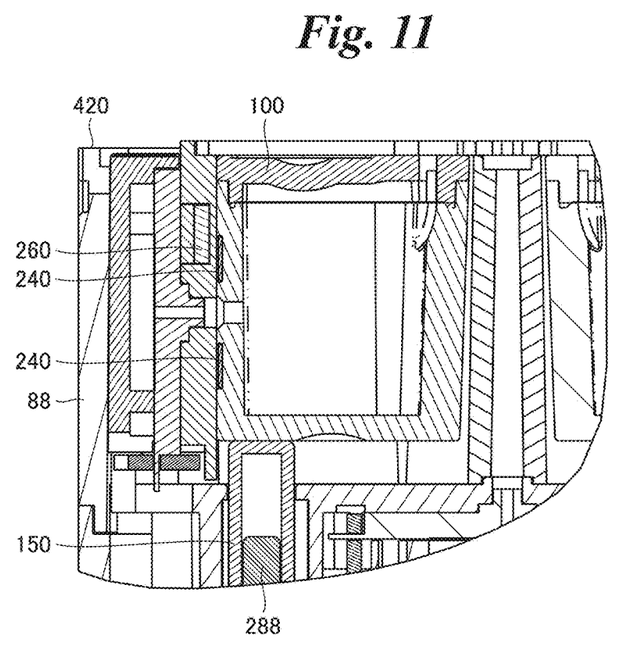
FIG. 11 is a cross-section of one side along 8-8 of the housing of aroma display shown in FIG. 3, illustrating how to remove an aroma cartridge.

When cartridge loading section is loaded with, for example, aroma cartridge 100 in this state, rod 150 is pressed by the lower surface of aroma cartridge 100 and moves downward. Thus, rotor 288 and rotor holder 286 also move downward. When the upper edges of stop members of rotor 288 reach the lower ends of the protruding portions formed on the inner surface of cam body 282, the upper edges of stop members move in the circumferential direction along the slopes on the lower surface of portions by the force of push-up spring 284. As a result, rotor 288 moves upward while rotating. When the upper edges of stop members reach the bottom portion of cam slopes (the uppermost portions of cam slopes), rotation of rotor 288 stops there, and the upper edges of stop members of rotor 288 engage with the bottom portion of cam slopes and stay there. As a result, rod 150 stops at a prescribed position where it slightly protrudes into the cartridge loading section. This position is referred to as the second position. At this second position, the length of that portion of rod 150 protruding into the cartridge loading section is shorter than that at the first position. As long as aroma cartridge 100 is held in cartridge loading section 130, the force from push-up spring 284 is not transmitted to rod 150, and rod 150 and aroma cartridge 100 remain at that position. This state is shown in FIG. 11.

Figure 9:
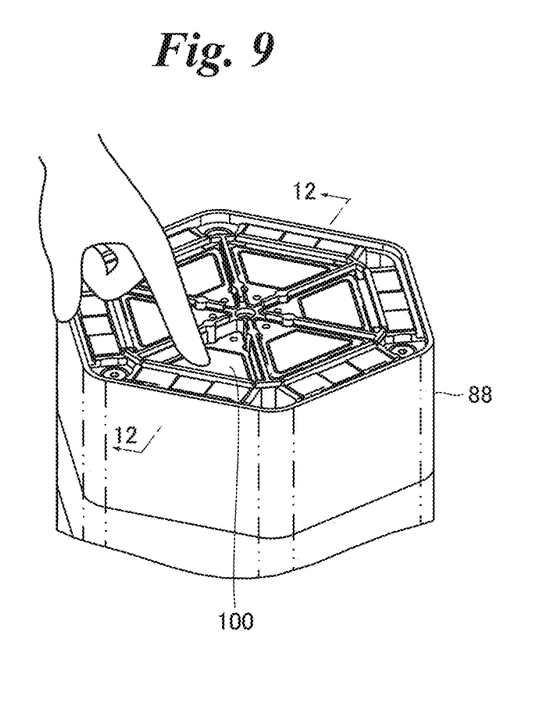
FIG. 9 is a perspective view of the housing of aroma display shown in FIG. 3, illustrating how to remove an aroma cartridge.
Figure 12:
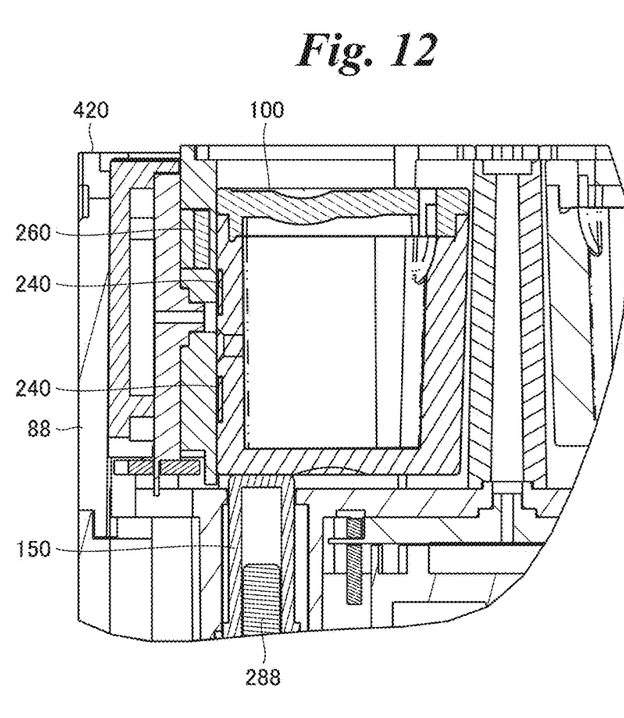
FIG. 12 is a cross-section along 12-12 of the housing of aroma display shown in FIG. 9, illustrating how to remove an aroma cartridge.

While aroma cartridge 100 is held in cartridge loading section 130, the upper surface of aroma cartridge 100 is substantially flush with upper surface 420 of upper body 88. When a user is to remove aroma cartridge 100, he/she pushes aroma cartridge 100 downward by his/her finger, as shown in FIG. 9. Then, referring to FIGS. 8 and 12, rod 150 and rotor 288 integrally move downward. When the upper edges of stop members of rotor 288 reach the lower ends of protruding portions of cam body 282, the upper edges of stop members also lower, causing the upper edges of stop members to pass the lowermost ends of cam slopes that they have engaged with so far at the protruded portions of cam body 282 and to move to the next cam slope, and further to move upward along the cam slopes while rotating in the circumferential direction along the cam slopes. Here, since there are recesses between the protruding portions formed in the inner circumference of cam body 282 ahead of the cam slopes, the stop members can move in the recesses along the longitudinal direction. Since rotor 288 is pushed upward by push-up spring 284, rotor 288 and rotor holder 286 move integrally upward and stop when the stop members reach the upper ends of the recesses within cam body 282. Rod 150 is pushed up by rotor 288. The end of rod 150 protrudes into cartridge loading section 130 and moves aroma cartridge 100 upward. This state is shown in FIG. 13.

Figure 10:
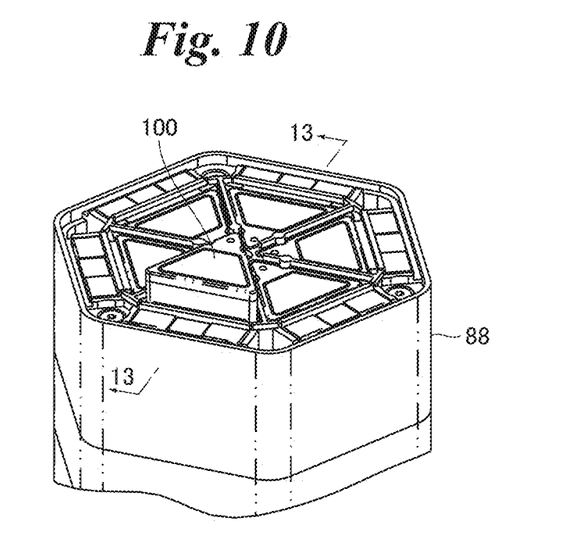
FIG. 10 is a perspective view of the housing of aroma display shown in FIG. 3, illustrating how to remove an aroma cartridge.
Figure 13:
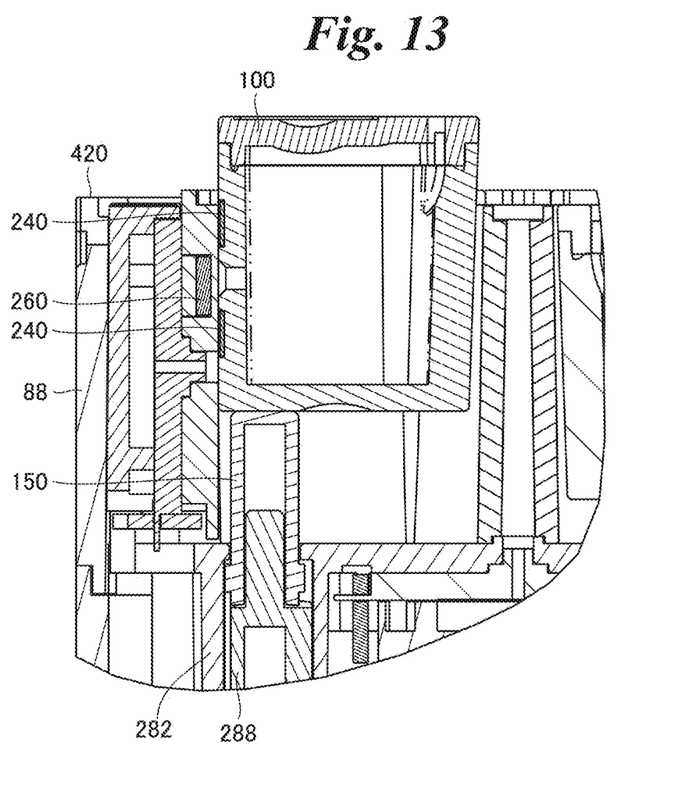
FIG. 13 is a cross-section along 13-13 of the housing of aroma display shown in FIG. 10, illustrating how to remove an aroma cartridge.

As a result, the upper end portion of aroma cartridge 100 is released from cartridge loading section 130 and protrudes from upper surface 420 of upper body 88 as shown in FIGS. 10 and 13. The user can hold the protruding upper end of aroma cartridge 100 and draw it from upper body 88.

If aroma display 50 is mounted facing downward or obliquely downward without the mechanism of metal plate 240 and magnet 260 or metal plate 246 and magnet 266 shown in FIG. 8, it is possible that aroma cartridge 100, 106 or the like falls as described above. As is apparent from FIGS. 11 and 13, however, by providing metal plate 240 and magnet 260 and the like, when aroma cartridge 100 is held in the cartridge loading section or when it is pushed out by rod 150 from the cartridge loading section, metal plate 240 and magnet 260 are at a position facing to each other. Therefore, because of the magnetic force acting therebetween, aroma cartridge 100 does not fall from upper body 88 but kept there. The user pushes the upper surface of aroma cartridge 100 so that aroma cartridge 100 is pushed out from the cartridge loading section, and by holding that portion of aroma cartridge 100 protruding from upper body 88, he/she can remove aroma cartridge 100 safely and easily.

Once aroma display 50 is loaded with necessary aroma cartridges, by individually or simultaneously operating micro blowers 180 to 190 and 322 of aroma display 50, it is possible to cause a desired scent or scents to be emitted from opening area 64 of cap 62. Control of micro blowers 180 to 190 and 322 is realized by transmitting control signals from an external control device to control board 340 through wireless communication.

Figure 14:
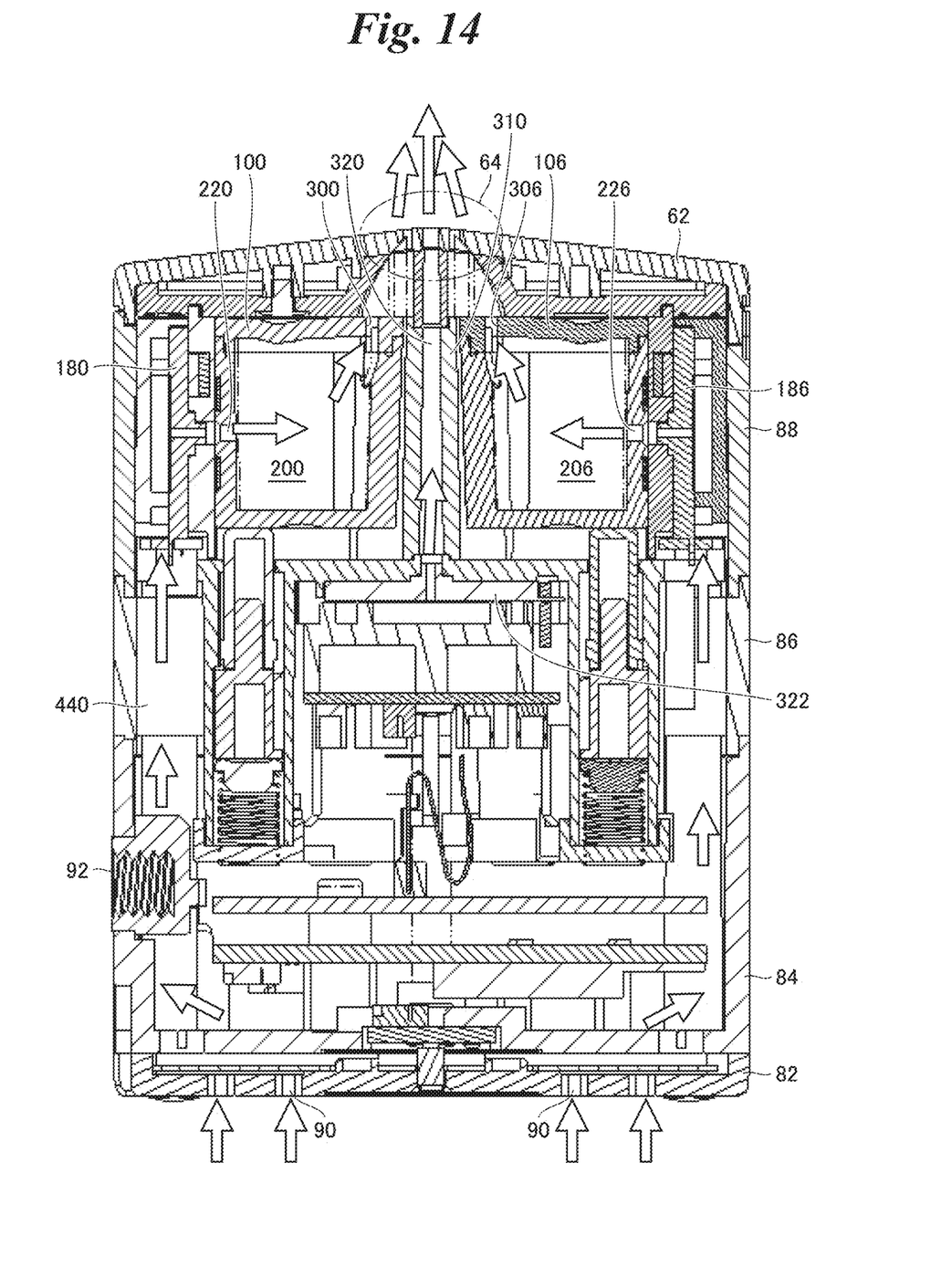
FIG. 14 is a cross-section along 14-14, illustrating air flows in the aroma display shown in FIG. 1.

FIG. 14 shows air flows when aroma display 50 operates. Referring to FIG. 14, by way of example, when the scent of aroma cartridge 100 is to be emitted, micro blower 180 is operated to introduce air through air feed inlet 220 of aroma cartridge 100 into the hollow portion 200 of aroma cartridge 100. At this time, the air is taken from openings 90 at the bottom of base panel 82, flows through air flow passage 440 on the left side to reach micro blower 180, and introduced from micro blower 180 into hollow portion 200 of aroma cartridge 100. The same applies to the aroma cartridge 106 shown on the right side of FIG. 14.

When the air is introduced to hollow portion 200 of aroma cartridge 100, the air containing scent (scented air) from the scent source sealed in aroma cartridge 100 is emitted through scent passage 300 into opening area 64.

On the other hand, micro blower 322 also blows the air taken in from openings 90 into emission opening 320 of duct member 310 and blows out the air to the outside of aroma display 50 through opening area 64. The scented air emitted from aroma cartridge 100 or the like is also carried by the air flow and spreads to locations away from aroma display 50.

The air emitted from opening area 64 through emission opening 320 of duct member 310 by driving micro blower 322 with AC voltage has a booster function for carrying the scented air from aroma cartridge 100 or the like farther away, and in addition, it has a function of dissipating scent previously emitted and lingering in the air. For this purpose, micro blower 322 preferably has a larger size and a structure capable of feeding a larger amount of air with higher strength than micro blower 180 and the like for feeding air into aroma cartridge 100 and the like. Further, by adjusting the air amount emitted from micro blower 322, it is possible to adjust density of scent emitted from opening area 64. Further, by adjusting the amount of air emitted from micro blower 322 and from micro blower 180 and the like, it is possible to implement a perfume blending function of the aroma display 50.

In the embodiment above, the number of cartridges that can be used at one time is six. The present invention, however, is not limited to such an embodiment. Provided that the opening for emitting scents can be formed in a very limited area, a larger number of aroma cartridges can be used. In the embodiment above, an example has been described in which a scent is emitted from a single aroma cartridge. The present invention, however, is not limited to such an embodiment. By emitting a plurality of different scents at one time, it is possible to mix and blend scents of aroma cartridges held by the aroma display to generate different scents. That is, perfume blending using any desired combination of a plurality of aroma cartridges is possible. Here, the combination includes use of only one aroma cartridge.

In the embodiment above, metal plate 240 is provided on the rear side of cartridge (opposite to the side where scent passage 300 is formed), and magnet 260 is provided at the corresponding position. The present invention, however, is not limited to such an embodiment. A metal plate as a magnetic body may be provided on an edge portion where scent passage 300 is formed or on another side surface of the cartridge, and a magnet may be provided on a corresponding position of the cartridge loading section.

Further, in aroma cartridge 100, it is desirable to provide a metal plate at least at that portion which is opposite to the side of cartridge loading section when aroma cartridge 100 is pushed out from cartridge loading section by rod 150. Therefore, in most cases, it is desirable to arrange the metal plate at any position on the lower half of the cartridge. Naturally, the metal plate may be positioned at any other portion.

Further, a magnet may be provided on the side of the cartridge and a metal plate may be provided on the side of the cartridge loading section. Though the magnet is a permanent magnet in the present embodiment, an electromagnet may be used on the side of the aroma display.

In the present embodiment, a magnet is embedded within the wall of cartridge loading section. This is to prevent too large a magnetic force between the magnet and the metal plate from making it difficult to remove, for example, aroma cartridge 100. The present invention, however, is not limited to such an embodiment. If a magnet having relatively weak magnetic force is used, the magnet may be exposed on the inner circumference of cartridge loading section.

The embodiments as have been described here are mere examples and should not be interpreted as restrictive. The scope of the present invention is determined by each of the claims with appropriate consideration of the written description of the embodiments and embraces modifications within the meaning of, and equivalence to, the languages in the claims.

DESCRIPTION OF REFERENCE CHARACTERS 50 aroma display
60, 360 housing
62 cap
64 opening area
82 base panel
84 base body
86 middle body
88 upper body
90 opening
92 screw hole
100, 102, 104, 106, 108, 110 aroma cartridge
130, 132, 134, 136, 138, 140 cartridge loading section
150, 152, 154, 156, 158, 160 rod
180, 186, 322 micro blower
200, 206 hollow portion
220, 226 air feed inlet
240, 246 metal plate
260, 266 magnet
280 knock mechanism
282 cam body
284 push-up spring
286 rotor holder
288 rotor
300, 306 scent passage 310 duct member
320 emission opening
340 control board
362, 420 upper surface
364 lower surface
366 side surface
440 air flow passage

What is claimed is:

1. An aroma cartridge used with an aroma display capable of holding and releasing a plurality of aroma cartridges and emitting a scent or scents from any combinations of said plurality of aroma cartridges, wherein
said aroma display includes
a housing having cartridge loading sections capable of holding said plurality of aroma cartridges, and
a mechanism provided in said housing for causing said plurality of aroma cartridges held in said cartridge loading sections to emit scent individually;
said cartridge loading section has an outer wall formed by a part of said housing and a bottom portion formed to be opposite to a bottom surface of said aroma cartridge held in said cartridge loading section;
said bottom portion has an opening;
said aroma display further includes
a knock mechanism, provided in said housing opposite to said cartridge loading section with respect to said bottom portion, having a rod retractably inserted to said cartridge loading section through said opening formed at said bottom portion, fixing said rod alternately at a first position at which tip end of said rod protrudes by a first distance into the cartridge loading section and a second position at which tip end of said rod protrudes by a second distance smaller than said first distance, in accordance with pressure on the tip end of the rod, and
a first ferromagnetic body provided at that position of said outer wall of said cartridge loading section which corresponds to the position where said aroma cartridge is held;
said aroma cartridge comprising:
a columnar housing having a first and a second surface having outer shapes parallel to and congruent with each other and a side surface connecting outer circumferences of the first and the second surface; wherein a hollow portion is formed in said columnar housing in which a scent source is sealed;
said columnar housing has formed therein a passage from said hollow portion to outside of said columnar housing and an air feed inlet for feeding air to the hollow portion from the outside of said columnar housing;
said aroma cartridge further comprising
a second ferromagnetic body fixed on at least a portion of said side surface; wherein
in response to feeding of air from said air feed inlet to said hollow portion, scented air from said scent source in said hollow portion is emitted through said passage to the outside.

2. The aroma cartridge according to claim 1, wherein
said outer shape has at least one corner;
said passage is opened close to said corner of said first surface, and
said second ferromagnetic body is provided on said side surface opposite to said corner.

3. An aroma display capable of holding and releasing a plurality of aroma cartridges and emitting a scent or scents from any combinations of said plurality of aroma cartridges, wherein
said plurality of aroma cartridges have ferromagnetic bodies on at least a part of their side surfaces;
said aroma display comprising:
a housing having cartridge loading sections for holding said plurality of aroma cartridges; and
a mechanism provided in said housing for individually causing each of said plurality of aroma cartridges held in said cartridge loading sections to emit scent; wherein
said cartridge loading section has an outer wall formed by a part of said housing and a bottom portion formed to be opposite to a bottom surface of said aroma cartridge held in said cartridge loading section; and
said bottom portion has an opening;
said aroma display further comprising:
a knock mechanism, provided in said housing opposite to said cartridge loading section with respect to said bottom portion, having a rod retractably inserted into said cartridge loading section through said opening formed at said bottom portion and an urging means urging the rod resiliently toward the cartridge loading section, fixing said rod alternately at a first position at which tip end of said rod protrudes by a first distance into the cartridge loading section and a second position at which tip end of said rod protrudes by a second distance smaller than said first distance, by the urging force from the urging means in accordance with pressure on the tip end of the rod; and
a ferromagnetic body provided on said outer wall such that said ferromagnetic body is opposite to said ferromagnetic body of said aroma cartridge when the aroma cartridge is held in said cartridge loading section.

4. The aroma display according to claim 3, wherein said aroma cartridge is held by magnetic force between said ferromagnetic body of said aroma cartridge and said ferromagnetic body of said outer wall, with at least an upper end portion of said aroma cartridge released from said cartridge loading section and protruding from said cartridge loading section.

5. The aroma display according to claim 4, wherein said aroma cartridge is held by magnetic force between said ferromagnetic body of said aroma cartridge and said ferromagnetic body of said aroma display when a tip end of said rod is at said first position.

6. The aroma display according to claim 5, wherein said aroma cartridge is held by magnetic force between said ferromagnetic body of said aroma cartridge and said ferromagnetic body of said aroma display when a tip end of said rod is at said second position.

7. The aroma display according to claim 4, wherein said aroma cartridge is held by magnetic force between said ferromagnetic body of said aroma cartridge and said ferromagnetic body of said aroma display when a tip end of said rod is at said second position.

8. The aroma display according to claim 3, wherein said aroma cartridge is held by magnetic force between said ferromagnetic body of said aroma cartridge and said ferromagnetic body of said aroma display when a tip end of said rod is at said first position.

9. The aroma display according to claim 8, wherein said aroma cartridge is held by magnetic force between said ferromagnetic body of said aroma cartridge and said ferromagnetic body of said aroma display when a tip end of said rod is at said second position.

10. The aroma display according to claim 3, wherein said aroma cartridge is held by magnetic force between said ferromagnetic body of said aroma cartridge and said ferromagnetic body of said aroma display when a tip end of said rod is at said second position.

\* \* \* \* \*